(12) United States Patent
Baek et al.

(10) Patent No.: US 8,246,790 B2
(45) Date of Patent: Aug. 21, 2012

(54) METHOD FOR COLLECTING (METH)ACRYLIC ACID AND APPARATUS FOR COLLECTING (METH)ACRYLIC ACID

(75) Inventors: Se-Won Baek, Daejeon (KR); Kyoung-Su Ha, Anyang-si (KR); Sung-Kyoo Park, Daejeon (KR); Jun-Seok Ko, Daejeon (KR); Dong-Hyun Woo, Daejeon (KR); Young-Bae Kim, Yeosu-si (KR); Jung-Hoon Chang, Yeosu-si (KR)

(73) Assignee: LG Chem, Ltd., Seoul (KR)

( * ) Notice: Subject to any disclaimer, the term of this patent is extended or adjusted under 35 U.S.C. 154(b) by 137 days.

(21) Appl. No.: 12/739,113

(22) PCT Filed: Oct. 23, 2008

(86) PCT No.: PCT/KR2008/006279
§ 371 (c)(1),
(2), (4) Date: Apr. 21, 2010

(87) PCT Pub. No.: WO2009/054688
PCT Pub. Date: Apr. 30, 2009

(65) Prior Publication Data
US 2010/0224478 A1    Sep. 9, 2010

(30) Foreign Application Priority Data
Oct. 23, 2007    (KR) .................. 10-2007-0106798

(51) Int. Cl.
*C07C 51/42* (2006.01)
(52) U.S. Cl. .............. 203/15; 562/600; 203/DIG. 21
(58) Field of Classification Search ............. 203/15, 203/16, 50, DIG. 21; 562/600
See application file for complete search history.

(56) References Cited

U.S. PATENT DOCUMENTS

| 3,932,500 | A | * | 1/1976 | Duembgen et al. | 562/600 |
| 4,618,709 | A |   | 10/1986 | Sada et al. | |
| 5,315,037 | A | * | 5/1994 | Sakamoto et al. | 562/545 |
| 5,785,821 | A |   | 7/1998 | Sakamoto et al. | |

(Continued)

FOREIGN PATENT DOCUMENTS

JP    56108727 A  *  8/1981 .................. 562/600

(Continued)

*Primary Examiner* — Robert A Hopkins
(74) *Attorney, Agent, or Firm* — McKenna Long & Aldridge LLP (57) ABSTRACT

The present invention provides a (meth)acrylic acid collecting method for collecting a (meth)acrylic acid from a mixed gas that includes an organic byproduct, a steam, and a (meth)acrylic acid that are generated in a production reaction of the (meth)acrylic acid, which includes the steps of a) contacting the mixed gas that includes the organic byproduct, the steam, and the (meth)acrylic acid with a (meth)acrylic acid absorption solvent to obtain a gas that includes the organic byproduct and the steam and the (meth)acrylic acid containing solution while the gas and the (meth)acrylic acid containing solution are separated from each other; b) contacting the gas that includes the organic byproduct and the steam that are obtained in the step a with the organic byproduct absorption solvent to obtain the gas that includes the steam and the organic byproduct containing solution while the gas and the organic byproduct containing solution are separated from each other; c) supplying the gas that includes the steam that is obtained in the step b into the production reaction of the (meth)acrylic acid; and d) obtaining the (meth)acrylic acid from the (meth)acrylic acid containing solution that is obtained in the step a while the (meth)acrylic acid and the (meth)acrylic acid containing solution are separated from each other, and a (meth)acrylic acid collecting device.

14 Claims, 2 Drawing Sheets

U.S. PATENT DOCUMENTS

| | | |
|---|---|---|
| 6,179,966 B1 | 1/2001 | Shimizu et al. |
| 6,339,817 B1 | 1/2002 | Maesako et al. |
| 6,395,140 B1 | 5/2002 | Herbst et al. |
| 6,399,817 B1 * | 6/2002 | Chapman et al. ............ 562/545 |
| 6,525,216 B1 | 2/2003 | Nishimura et al. |
| 6,667,419 B1 * | 12/2003 | Matsumoto et al. .......... 562/600 |
| 7,258,766 B2 | 8/2007 | Yada et al. |
| 2004/0249202 A1 * | 12/2004 | Hirao et al. ................... 562/545 |
| 2005/0176997 A1 | 8/2005 | Yada et al. |
| 2005/0192464 A1 * | 9/2005 | Kang et al. .................... 562/600 |
| 2006/0025629 A1 * | 2/2006 | Kang et al. .................... 562/600 |

FOREIGN PATENT DOCUMENTS

JP  09-157213 A  6/1997

* cited by examiner

METHOD FOR COLLECTING (METH)ACRYLIC ACID AND APPARATUS FOR COLLECTING (METH)ACRYLIC ACID

TECHNICAL FIELD

The present invention relates to a method of collecting a (meth)acrylic acid from a mixed gas that includes an organic byproduct, a steam and a (meth)acrylic acid generated during the production reaction of the (meth)acrylic acid, and an apparatus for collecting the same.

This application is a 35 U.S.C. §371 National Stage entry of International Application No. PCT/KR2008/006279, filed on Oct. 23, 2008, and claims priority to Korean Application No. 10-2007-0106798, filed on Oct. 23, 2007, which are all hereby incorporated by reference in their entireties.

BACKGROUND ART

Generally, an acrylic acid may be obtained by a gas phase catalytic oxidation reaction of one or more selected from propane, propylene, isobutylene, and acrolein.

For example, under the presence of an appropriate catalyst in a reactor, propylene or propane is converted through acrolein into the acrylic acid, and at a rear part of the reactor, the mixed gas that includes the acrylic acid, unreacted propylene or propane, acrolein, an inert gas, carbon dioxide, a steam and various reaction organic byproducts is obtained.

Generally, the mixed gas is cooled or contacted with water in an absorbing column to dissolve soluble components such as the acrylic acid in the mixed gas to obtain the aqueous solution including the acrylic acid, and to discharge non-soluble gas in the mixed gas to the upper part of the absorbing column to recycle the gas to the reactor or convert the gas through an incineration furnace into harmless gas for discharging.

The acrylic acid aqueous solution is provided through a stripping column into a azeotropic distillation column, the acrylic acid among the acrylic acid aqueous solution that is provided into the azeotropic distillation column is obtained in a high concentration of acrylic acid at a lower part of the column of the azeotropic distillation column. In addition, water and the organic byproduct among the acrylic acid aqueous solution that forms the azeotrope in conjunction with an appropriate azeotropic agent in the azeotropic distillation column is discharged to the upper part of the column of the azeotropic distillation column to be recycled into the acrylic acid absorbing column or wasted.

Generally, according to the type of azeotropic agent that is used in the azeotropic distillation column, the separation method of the azeotropic agent, the operation method of the separation column at a rear part of the water separation process, and the treatment method of water separated in the azeotropic distillation column are significantly changed.

For example, Japanese Unexamined Patent Application Publication No. 1997-157213 discloses a method of directly providing a water layer obtained in an azeotropic distillation column into an acrylic acid absorbing column without a solvent recovery column to obtain an acrylic acid aqueous solution. Here, the waste water that is generated in the azeotropic distillation column and includes 0.5-5.0% by weight of the acrylic acid, 3-10% by weight of the acetic acid, and 0.01-0.5% by weight of the distillation solvent is recycled into the acrylic acid absorbing column to highly efficiently absorb the acrylic acid.

DISCLOSURE OF INVENTION

Technical Problem

However, in the case of Japanese Unexamined Patent Application Publication No. 1997-157213, since the distillation solvent that is the acetic acid and the volatile organic compound in a waste water is present in an excessive amount, the concentration of waste in the off-gas that is discharged from the acrylic acid absorbing column may be increased, in the case of when this gas is supplied to the reactor, the impurity organic compound such as the acetic acid and the organic solvent included therein rapidly deactivates the catalyst in the reactor or produces a large amount of byproducts to cause a loss of the gas phase catalytic oxidation reaction in the reactor.

In order to solve this, U.S. Pat. No. 6,399,817 discloses a method of supplying a waste water that is discharged from an azeotropic distillation column into an acrylic acid absorbing column after a concentration of the acetic acid in a waste water is reduced in less than 3.0% by weight by using a stripper.

However, in the case of U.S. Pat. No. 6,399,817, when the off-gas that is discharged from the acrylic acid absorbing column is supplied into the reactor, it is required that the acetic acid that is included in the off-gas does not affect the gas phase catalytic oxidation reaction in the reactor. However, there is a problem in that by using the disclosed method, it is not easy to sufficiently remove the acetic acid among the off-gases and provide it into the reactor, and among the absorption solvents provided into the acrylic acid absorbing column, in order to maintain the content of the acetic acid to less than 3% by weight, the relatively large stripper is required.

Technical Solution

The present invention provides a (meth)acrylic acid collecting method for collecting a (meth)acrylic acid from a mixed gas that includes an organic byproduct, a steam, and a (meth)acrylic acid that are generated in a production reaction of the (meth)acrylic acid, which includes the steps of a) contacting the mixed gas that includes the organic byproduct, the steam, and the (meth)acrylic acid with a (meth)acrylic acid absorption solvent to obtain a gas that includes the organic byproduct and the steam and the (meth)acrylic acid containing solution while the gas and the (meth)acrylic acid containing solution are separated from each other; b) contacting the gas that includes the organic byproduct and the steam that are obtained in the step a with the organic byproduct absorption solvent to obtain the gas that includes the steam and the organic byproduct containing solution while the gas and the organic byproduct containing solution are separated from each other; c) supplying the gas that includes the steam that is obtained in the step b into the production reaction of the (meth)acrylic acid; and d) obtaining the (meth)acrylic acid from the (meth)acrylic acid containing solution that is obtained in the step a while the (meth)acrylic acid and the (meth)acrylic acid containing solution are separated from each other.

The present invention provides a (meth)acrylic acid collecting device for collecting a (meth)acrylic acid from the mixed gas that includes the organic byproduct, the steam, and the (meth)acrylic acid that are generated in a reactor for producing the (meth)acrylic acid, which includes a (meth) acrylic acid absorbing column that is connected to the reactor to contact the mixed gas that includes the organic byproduct, the steam, and the (meth)acrylic acid that are discharged from the reactor with a (meth)acrylic acid absorption solvent to be separated into a gas that includes the organic byproduct and the steam and a (meth)acrylic acid containing solution; an organic byproduct absorbing column that is connected to the (meth)acrylic acid absorbing column to contact the gas that includes the organic byproduct and the steam that are discharged from the (meth)acrylic acid absorbing column with the organic byproduct absorption solvent to be separated into the gas that includes the steam and the organic byproduct containing solution; a reaction gas transport line that connects the organic byproduct absorbing column to the reactor and transports the gas that includes the steam that is discharged from the organic byproduct absorbing column to the reactor so that the gas that includes the steam is used as the reaction gas for production of the (meth)acrylic acid in the reactor; and a (meth)acrylic acid separating device that is connected to the (meth)acrylic acid absorbing column and separates and obtains the (meth)acrylic acid from the (meth)acrylic acid containing solution that is discharged from the (meth)acrylic acid absorbing column.

Advantageous Effects

According to the present invention, in a gas that includes an organic byproduct and a steam, after an organic byproduct is sufficiently removed, it is provided into a (meth)acrylic acid production reactor and can be reused as the reaction gas. Accordingly, in the case of when the gas in which a conventional organic byproduct is not sufficiently removed is supplied into the reactor, the occurrence of process troubles by the organic byproduct included in the gas is capable of being prevented.

In addition, in the case of when the (meth)acrylic acid is produced by using the catalyst in the (meth)acrylic acid production reactor, in the case of the used catalyst, steam is required in order to perform the stable operation, and at this time, in the gas that includes the organic byproduct and the steam, the organic byproduct is sufficiently removed and the gas that includes steam is capable of being supplied into the (meth)acrylic acid production reactor. Accordingly, a steam type of a process water that is added into the initial reactor is capable of being saved. In addition, a spot in which the temperature is abnormally high or heat accumulation is relatively high in the catalyst in the reactor, that is, a hot spot may occur. This hot spot is capable of being reduced to improve the stability of the catalyst and to improve the reaction yield.

In addition, as a (meth)acrylic acid absorption solvent that is used in order to obtain the (meth)acrylic acid that is included in the mixed gas including an organic byproduct, a steam, and a (meth)acrylic acid as a (meth)acrylic acid containing solution, in the case of when the organic byproduct containing solution is used, the yield ratio of the (meth) acrylic acid is capable of being improved.

BEST MODE FOR CARRYING OUT THE INVENTION

A (meth)acrylic acid collecting method for collecting a (meth)acrylic acid from a mixed gas that includes an organic byproduct, a steam, and a (meth)acrylic acid that are generated in a production reaction of the (meth)acrylic acid according to the present invention includes the steps of a) contacting the mixed gas that includes the organic byproduct, the steam, and the (meth)acrylic acid with a (meth)acrylic acid absorption solvent to obtain a gas that includes the organic byproduct and the steam and the (meth)acrylic acid containing solution while the gas and the (meth)acrylic acid containing solution are separated from each other; b) contacting the gas that includes the organic byproduct and the steam that are obtained in the step a with the organic byproduct absorption solvent to obtain the gas that includes the steam and the organic byproduct containing solution while the gas and the organic byproduct containing solution are separated from each other; c) supplying the gas that includes the steam that is obtained in the step b into the production reaction of the (meth)acrylic acid; and d) obtaining the (meth)acrylic acid from the (meth)acrylic acid containing solution that is obtained in the step a while the (meth)acrylic acid and the (meth)acrylic acid containing solution are separated from each other.

In the step a, the mixed gas that includes the organic byproduct, the steam, and the (meth)acrylic acid and the (meth)acrylic acid absorption solvent may be contacted with each other in the (meth)acrylic acid absorbing column.

The upper temperature of the (meth)acrylic acid absorbing column may be in the range of 50 to 70° C.

The (meth)acrylic acid absorbing column may be a packed column in which a filling agent is included or various general multistaged columns.

Here, examples of the filling agent may include a Rashing ring, Pall ring, a Saddle, a Gauze, and a Structured packing.

Only a portion of the mixed gas that includes the organic byproduct, the steam, and the (meth)acrylic acid that is obtained in the step a is supplied into the step b, and the remains may be wasted.

In the case of when a low boiling point substance is included in the (meth)acrylic acid containing solution that is obtained in the step a, after the (meth)acrylic acid containing solution that is obtained in the step a is supplied into a stripping column to remove the low boiling point substance, and the (meth)acrylic acid containing solution that is obtained in the step a may be supplied into the step d.

The stripping column may be a packed column in which a filling agent is included or various general multistaged columns.

The low boiling point substance that is stripped from the stripping column may be acrolein.

In the step b, the mixed gas that includes the organic byproduct and the steam obtained in the step a and the organic byproduct absorption solvent may be contacted with each other in the organic byproduct absorbing column.

Here, as the organic byproduct, an acetic acid may be exemplified, and in the case of when the organic byproduct is the acetic acid, the organic byproduct absorbing column may be an acetic acid absorbing column.

The upper and the lower temperatures of the acetic acid absorbing column may be in the range of 50 to 70° C., and the upper and the lower temperatures of the acetic acid absorbing column may be the same as or slightly lower than the upper temperature of the (meth)acrylic acid absorbing column.

The acetic acid absorbing column may be a packed column in which a filling agent is included or various general multistaged columns.

Here, examples of the filling agent may include a Rashing ring, Pall ring, a Saddle, a Gauze, and a Structured packing.

As the organic byproduct absorption solvent that is supplied into the acetic acid absorbing column, water may be used.

The temperature of the organic byproduct absorption solvent that is supplied into the organic byproduct absorbing column may be in the range of 15 to 70° C.

The (meth)acrylic acid collecting method may further includes supplying the organic byproduct containing solution that is obtained in the step b into the step a so as to be used as the (meth)acrylic acid absorption solvent of the step a.

The temperature of the organic byproduct containing solution that is obtained in the step b and supplied in the step a as the (meth)acrylic acid absorption solvent of the step a may be in the range of a normal temperature to the upper temperature of the (meth)acrylic acid absorbing column. For example, the temperature of the organic byproduct containing solution may be in the range of 15 to 70° C.

The organic byproduct containing solution that is obtained in the step b is supplied into the step a absorbs the (meth)acrylic acid that is included in the mixed gas that includes the organic byproduct, the steam, and the (meth)acrylic acid and is obtained in the step a to function to obtain the (meth)acrylic acid that is included in the gas in an aqueous solution state. That is, it is used as the (meth)acrylic acid absorption solvent of the step a. In the case of when the organic byproduct containing solution is used as the (meth)acrylic acid absorption solvent, as compared to the case of when a water is used as the (meth)acrylic acid absorption solvent, an absorption ratio of the (meth)acrylic acid is capable of being remarkably improved.

The concentration of the organic byproduct of the organic byproduct containing solution that is obtained in the step b may be in the range of 3-50% and preferably 3~20%.

In the case of when the organic byproduct that is not separated in the step b is included in the gas that includes the steam obtained in the step b, the concentration of the organic byproduct of the gas that includes the steam obtained in the step b may be in the range of 0 to 1000 ppm and preferably 0 to 500 ppm.

In the step c, the gas in which the organic byproduct is almost completely removed and the water is included is supplied in the production reaction step of the (meth)acrylic acid so as to be used in the production reaction of the (meth)acrylic acid. Accordingly, the occurrence of the production reaction troubles of the (meth)acrylic acid by the organic byproduct by supplying the gas in which the conventional organic byproduct is not sufficiently removed and the content of the organic byproduct is high into the production reaction of the (meth)acrylic acid is capable of being prevented.

In addition, in the production reactor of the (meth)acrylic acid, in the course of producing the (meth)acrylic acid by using the catalyst, in the case of the used catalyst, steam is required in order to perform the stable operation. At this time, in the gas that includes the organic byproduct and the steam, the gas in which the organic byproduct is sufficiently removed and the steam is included is capable of being supplied into the production reactor of the (meth)acrylic acid. Accordingly, the number of steam type processes that are added to the initial reactor is capable of being saved. In addition, a spot in which the temperature is abnormally high or heat accumulation is relatively high in the catalyst in the reactor, that is, a hot spot may occur. This hot spot is capable of being reduced to improve the stability of the catalyst and to improve the reaction yield.

The production method of the (meth)acrylic acid is performed in the reactor in which one or more reactants selected from the group consisting of propane, propylene, isobutylene, t-butylene, butane, and (meth)acrolein are subjected to the oxidation reaction under the catalyst, and in the step c, the gas that includes the steam obtained in the step b is supplied into the reactor.

The content of the steam of the gas that includes the steam obtained in the step b, which is supplied into the reactor so as to be used in the production reaction of the (meth)acrylic acid may be in the range of 7 to 15% on the basis of the total amount added into the reactor, that is, the content of the raw material including the reactants and the gases that include the steam added to the reactor, which is obtained in the step b.

As the catalyst, a catalyst that is disclosed in Korean Registered Patent Nos. 0349602 and 0378018 may be used.

For example, the catalyst may be a catalyst that is represented by the following Formula 1 in order to produce (meth)acrolein that is an example of unsaturated aldehyde.

$$Mo_aBi_bFe_cX_dY_eZ_fO_g \quad \text{(Formula 1)}$$

wherein X is one or more elements that are selected from Co and Ni,

Y is one or more elements that are selected from Li, Na, K, Rb, Cs and Tl,

Z is one or more elements that are selected from W, Be, Mg, S, Ca, Sr, Ba, Te, Se, Ce, Ge, Mn, Cr, Ag, Sb, Pb, As, B, P, Nb, Cu, Cd, Sn, Al, Zr, Ti and Si, and a, b, c, d, e, f and g are atom ratios of the elements, when a is 12, b=0.1~20, c=0.1~20, d=0.52~20, e=0.01~2 and f=0~10 on the basis of a, and g is an atom number of oxygen required to satisfy atomic values of the components.

In addition, the catalyst may be a catalyst that is represented by the following Formula 2 in order to produce (meth)acrolein that is an example of unsaturated aldehyde.

$$Mo_aW_bV_cA_dB_eO_x \quad \text{(Formula 2)}$$

wherein Mo is molybdenum, W is tungsten, and V is vanadium,

A is one or more elements that are selected from the group consisting of iron, copper, bismuth, chrome, tin, antimony and potassium, B is one or more elements that are selected from the group consisting of alkali earth metals O is oxygen, a, b, c, d, e and x are atom ratios of Mo, W, V, A, B and 0, when a is 10, b=1.5~4, c=1~5, d=1~4, e=O~2 on the basis of a, and x is an a value that is determined according to an oxidation state of other elements.

In the step d, the distillation method may be used.

In the case of when the organic byproduct that is not separated in the step a is included in the (meth)acrylic acid containing solution that is obtained in the step a, in the step d, the (meth)acrylic acid containing solution that is obtained in the step a is separated into the organic byproduct containing solution and the (meth)acrylic acid by the distillation method and obtained.

The (meth)acrylic acid collecting method may further include supplying the organic byproduct containing solution that is obtained in the step d into the step a so as to be used as the (meth)acrylic acid absorption solvent of the step a.

In the case of when the (meth)acrylic acid that is not separated in the step d is included in the organic byproduct containing solution that is obtained in the step d, the concentration of the organic byproduct of the organic byproduct containing solution may be in the range of 3 to 50%, and the concentration of the (meth)acrylic acid may be in the range of 0 to 5%.

In the step d, the distillation method is an azeotropic distillation method in which an azeotropic distillation column in which an azeotropic agent is supplied is used, and in the case of when water, the organic byproduct, and the azeotropic agent that are not separated in the step d are included in the (meth)acrylic acid that is obtained in the step d by using the azeotropic distillation method, the concentration of the water of the (meth)acrylic acid that is obtained in the step d may be in the range of 0 to 1%, the concentration of the organic byproduct may be in the range of 0 to 1%, and the concentration of the azeotropic agent may be in the range of 0 to 0.05%. Here, preferably, the concentrations of the water and the organic byproduct are may be in the range of 0 to 0.1%, and more preferably 0 to 0.05%, and the concentration of the azeotropic agent may be in the range of 0 to 0.001%.

The (meth)acrylic acid collecting method may further include, in the step d, a distillation method. The distillation method is an azeotropic distillation method in which an azeotropic distillation column in which an azeotropic agent is supplied is used. When the azeotropic agent is included in the organic byproduct containing solution that is obtained in the step d, the organic byproduct containing solution from the azeotropic distillation column is supplied to a phase separator to separate the azeotropic agent from the organic byproduct containing solution; and the organic byproduct containing solution from which the azeotropic agent is removed from the phase separator is supplied into the step a to use the organic byproduct containing solution as the (meth)acrylic acid absorption solvent of the step a.

The azeotropic distillation column may be a packed column in which a filling agent is included or various general multistaged columns.

A tray column (sieve tray column) may be used as the azeotropic distillation column, and in the case of when this is used, the azeotropic agent that is capable of forming the azeotrope in conjunction with water may be added to the upper part of the column to break the azeotrope of the (meth) acrylic acid-water to obtain water and the azeotropic agent at the upper part of the column and to obtain the pure (meth) acrylic acid at the lower part of the column.

The azeotropic agent that is used in the azeotropic distillation column may be one or more solvents that are selected from aliphatics, aromatics, and halogenated hydrocarbons. However, this is not limited thereto.

The phase separator is an apparatus for separating the liquid phases that are not mixed with each other, and may be largely classified into an apparatus using a gravity force and an apparatus using a centrifugal force. In the case of the general apparatus using the gravity force, the discharge ports are provided at an upper and a lower part thereof, and the light liquid may be discharged through the upper part thereof and the heavy liquid may be discharged through the lower part thereof to separate the liquid phases.

All of the solution containing organic byproduct, which is discharged from the phase separator, may be supplied into the (meth)acrylic acid absorbing column and some of them may be wasted.

The (meth)acrylic acid collecting method may further include supplying the azeotropic agent that is separated in the phase separator into the azeotropic distillation column.

The concentration of the organic byproduct of the organic byproduct containing solution that is supplied from the phase separator into the step a may be in the range of 3 to 50%.

In the case of when the azeotropic agent that is not removed is included in the organic byproduct containing solution that is discharged from the phase separator, after the azeotropic agent that is not removed and included in the organic byproduct containing solution that is discharged from the phase separator is removed at a solvent recovery column, the organic byproduct containing solution may be supplied into the step a.

The solvent recovery column may be a packed column in which a filling agent is included or various general multistaged columns.

The solvent recovery column may be a multistaged distillation column, and since the solvent is generally more light, the solvent may be collected at the upper part of the column.

The (meth)acrylic acid collecting method may further include supplying the azeotropic agent that is separated in the solvent recovery column into the phase separator.

The (meth)acrylic acid collecting method may further include, in the case of when the high boiling point impurity is included in the (meth)acrylic acid that is obtained in the step d, supplying the (meth)acrylic acid that is obtained in the step d into the high boiling point separation column to remove the high boiling point impurity.

The high boiling point separation column may be a packed column in which a filling agent is included or various general multistaged columns.

The high boiling point separation column may be a general distillation column, and the impurity that has the high boiling point may be condensed at the lower part of the column and then discharged and the pure (meth)acrylic acid may be obtained at the upper part of the column.

Examples of the high boiling point impurity that is separated in the high boiling point separation column may include an acrylic acid dimer, a maleic acid, a maleic acid anhydride, and a polymerization inhibitor.

The (meth)acrylic acid collecting method may further include a purifying step of purifying a crude acrylic acid that is obtained in the high boiling point separation column. The crude acrylic acid means is a CAA (Crude acrylic acid), and means an acrylic acid that has the purity capable of synthesizing acrylic acid ester.

Through the purifying step, the high purity acrylic acid is capable of being obtained.

The high purity acrylic acid is a HPAA (High Purity Acrylic acid), and is a high purity product that is purified one more as compared to the CAA.

The high boiling point impurity that is obtained in the high boiling point separation column is obtained in a waste oil form, and may be introduced into a dimer separator in order to efficiently configure a process.

In the dimer separator, the acrylic acid dimer and the like are partially decomposed into the acrylic acid monomers and then collected, and the remains are incinerated as the waste oil.

Meanwhile, a (meth)acrylic acid collecting device for collecting a (meth)acrylic acid from the mixed gas that includes the organic byproduct, the steam, and the (meth)acrylic acid that are generated in a reactor for producing the (meth)acrylic acid according to the present invention includes a (meth) acrylic acid absorbing column that is connected to the reactor to contact the mixed gas that includes the organic byproduct, the steam, and the (meth)acrylic acid that are discharged from the reactor with a (meth)acrylic acid absorption solvent to be separated into a gas that includes the organic byproduct and the steam and a (meth)acrylic acid containing solution; an organic byproduct absorbing column that is connected to the (meth)acrylic acid absorbing column to contact the gas that includes the organic byproduct and the steam that are discharged from the (meth)acrylic acid absorbing column with the organic byproduct absorption solvent to be separated into the gas that includes the steam and the organic byproduct containing solution; a reaction gas transport line that connects the organic byproduct absorbing column to the reactor and transports the gas that includes the steam that is discharged from the organic byproduct absorbing column to the reactor so that the gas that includes the steam is used as the reaction gas for production of the (meth)acrylic acid in the reactor; and a (meth)acrylic acid separating device that is connected to the (meth)acrylic acid absorbing column and separates and obtains the (meth)acrylic acid from the (meth)acrylic acid containing solution that is discharged from the (meth)acrylic acid absorbing column.

The (meth)acrylic acid collecting device may further includes a (meth)acrylic acid absorption solvent supply line that connects the organic byproduct absorbing column to the (meth)acrylic acid absorbing column and supplies the organic byproduct containing solution that is discharged from the organic byproduct absorbing column from the organic byproduct absorbing column to the (meth)acrylic acid absorbing column so that the organic byproduct containing solution is capable of being used as the (meth)acrylic acid absorption solvent of the (meth)acrylic acid absorbing column.

The (meth)acrylic acid collecting device may further include a stripping column that is positioned between the (meth)acrylic acid absorbing column and the (meth)acrylic acid separating device, and in the case of when a low boiling point substance is included in the (meth)acrylic acid containing solution that is discharged from the (meth)acrylic acid absorbing column, removes the low boiling point substance from the (meth)acrylic acid containing solution that is discharged from the (meth)acrylic acid absorbing column to supply the (meth)acrylic acid containing solution into the (meth)acrylic acid separating device.

The (meth)acrylic acid separating device comprises an azeotropic distillation column using the azeotropic agent, and the azeotropic distillation column, in the case of when the organic byproduct that is not separated in the (meth)acrylic acid absorbing column is included in the (meth)acrylic acid containing solution that is discharged from the (meth)acrylic acid absorbing column, separates the (meth)acrylic acid containing solution that is discharged from the (meth)acrylic acid absorbing column into the organic byproduct containing solution and the (meth)acrylic acid.

The (meth)acrylic acid collecting device may further include a phase separator that is connected to the azeotropic distillation column, and in the case of when the azeotropic agent of the azeotropic distillation column is included in the organic byproduct containing solution that is discharged from the azeotropic distillation column, separates the azeotropic agent from the organic byproduct containing solution that is discharged from the azeotropic distillation column; and a (meth)acrylic acid absorption solvent supply line that connects the phase separator to the (meth)acrylic acid absorbing column and supplies the organic byproduct containing solution that is discharged from the phase separator into the (meth)acrylic acid absorbing column so that the organic byproduct containing solution that is discharged from the phase separator is used as the (meth)acrylic acid absorption solvent of the (meth)acrylic acid absorbing column.

The (meth)acrylic acid collecting device may further include an azeotropic agent supply line that connects the phase separator to the azeotropic distillation column and allows to supply the azeotropic agent that is discharged from the phase separator into the azeotropic distillation column.

The (meth)acrylic acid collecting device may further include a solvent recovery column that is positioned between the phase separator and the (meth)acrylic acid absorbing column, and in the case of when the azeotropic agent that is not removed in the phase separator is included in the organic byproduct containing solution that is discharged from the phase separator, removes the azeotropic agent that is not removed and is included in the organic byproduct containing solution that is discharged from the phase separator to supply the organic byproduct containing solution into the (meth)acrylic acid absorbing column.

The (meth)acrylic acid collecting device may further include an azeotropic agent discharge line that connects the solvent recovery column with the phase separator and supplies the azeotropic agent, which is separated from the solvent recovery column, into the phase separator.

The (meth)acrylic acid collecting device may further include a high boiling point separation column that is connected to the (meth)acrylic acid separating device, and in the case of when the high boiling point impurity is included in the (meth)acrylic acid that is discharged from the (meth)acrylic acid separating device, removes the high boiling point impurity from the (meth)acrylic acid that is discharged from the (meth)acrylic acid separating device.

Hereinafter, the present invention will be described in detail with reference to the accompanying drawings.

The production reaction of the acrylic acid is performed in the reactor (which is not shown). That is, one or more that are selected from propane, propylene, isobutylene, acrolein in the reactor are capable of being subjected to the gas phase catalytic oxidation reaction to obtain the acrylic acid. In the case of when the acrylic acid is produced by using this method, at a rear part of the reactor, the mixed gas that includes an acrylic acid; unreacted propane, propylene, isobutylene, and/or acrolein; an inert gas; carbon dioxide; a steam; and various reaction organic byproducts is obtained. Here, the type of the organic byproducts that are included in the mixed gas may be various, but the case of when the organic byproduct is the acetic acid will be described as an example hereinafter. However, this is limited thereto.

As described above, the method for collecting the acrylic acid according to a first embodiment of the present invention, in which the acrylic acid is collected from the mixed gas 1 that is generated in the production reaction of the acrylic acid, will be described with reference to the accompanying FIG. 1.

Figure 1:
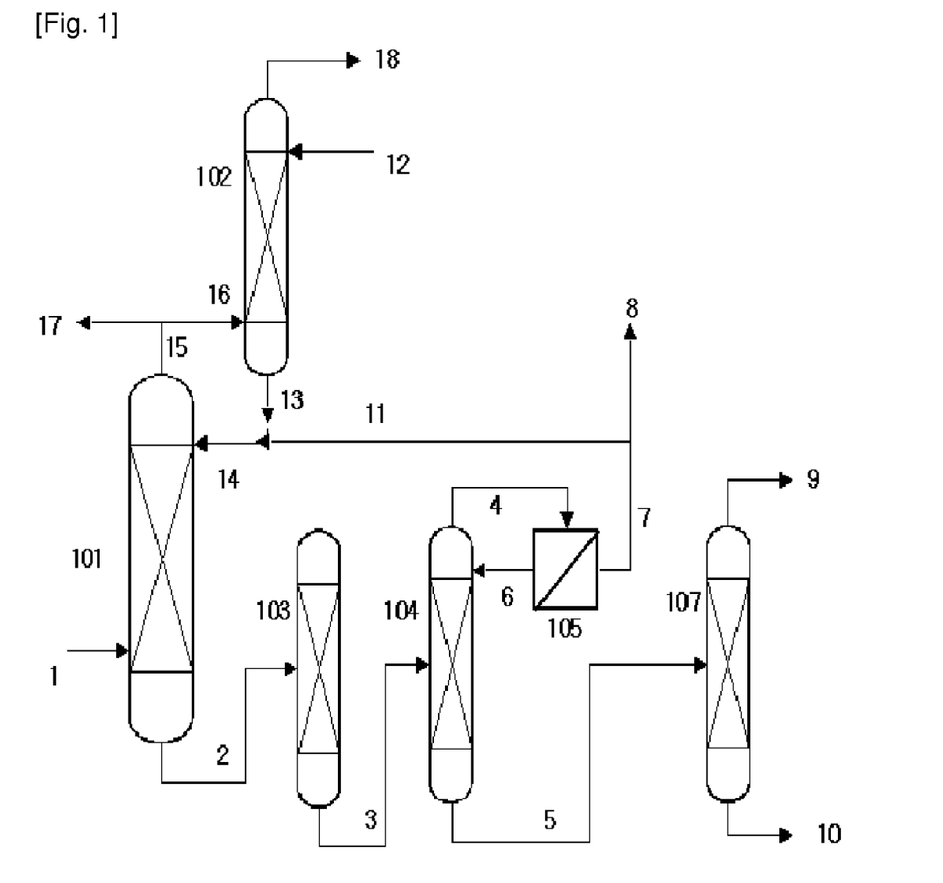
FIG. 1 is a view that schematically illustrates a process for collecting an acrylic acid according to a first embodiment of the present invention.

The mixed gas 1 that is generated in the production reaction of the acrylic acid is discharged from the reactor as shown in FIG. 1 to be provided into the lower part of the column of the acrylic acid absorbing column 101.

Here, the first absorption solvent is supplied through the first absorption solvent input line 14 that is positioned at the upper part of the acrylic acid absorbing column 101 into the acrylic acid absorbing column 101.

The first absorption solvent that is supplied through the first absorption solvent input line 14 into the acrylic acid absorbing column 101 is discharged from the acetic acid absorbing column 102 is an acetic acid containing aqueous solution that is transported through an acetic acid containing aqueous solution transport line 13 that is the (meth)acrylic acid absorption solvent supply line, discharged from the acetic acid containing aqueous solution and/or phase separator 105, and transported through the acetic acid containing aqueous solution transport line 11 that is another (meth)acrylic acid absorption solvent supply line, and the concentration of the acetic acid of the first absorption solvent may be 3% or more.

Accordingly, if the acetic acid containing first absorption solvent and the mixed gas 1 that are supplied through the first absorption solvent input line 14 meet each other in the inside of the acrylic acid absorbing column 101, the acrylic acid that is included in the mixed gas 1 is absorbed in the acetic acid containing first absorption solvent to be discharged in an aqueous solution form, that is, in an acrylic acid containing aqueous solution through the lower part of the column of the acrylic acid absorbing column 101.

In addition, since the acrylic acid that is included in the mixed gas 1 is absorbed in the acetic acid containing first absorption solvent, the acrylic acid that is included in the mixed gas is removed, but the mixed gas that includes various other gases and the acetic acid that is the organic byproduct is discharged through the discharge line 15 that is positioned on the column of the acrylic acid absorbing column 101.

A portion gas of the gas that is discharged from the discharge line 15 is moved through the gas waste line 17 into an incinerator (which is not shown), and discarded after waste heat is collected. Another portion gas is supplied through the gas input line 16 into the acetic acid absorbing column 102.

If the gas that is added into the acetic acid absorbing column 102 and a process water 12 that is supplied into the inside of the acetic acid absorbing column 102 meet each other in the inside of the acetic acid absorbing column 102, the acetic acid that is included in the gas that is supplied through the gas input line 16 into the acetic acid absorbing column 102 is absorbed in the process water 12 and then is discharged in an aqueous solution form, that is, in an acetic acid containing aqueous solution form through the lower part of the column of the acetic acid absorbing column 102.

As described above, the acetic acid containing aqueous solution is used as the acetic acid containing first absorption solvent of the acrylic acid absorbing column 101 through the acetic acid containing aqueous solution transport line 13.

Here, the acrylic acid that is not absorbed by the acetic acid containing first absorption solvent of the acrylic acid absorbing column 101 may be included in the gas that is inputted through the gas input line 16 into the acetic acid absorbing column 102, and in this case, it may be absorbed in conjunction with the acetic acid in the process water 12 in the inside of the acetic acid absorbing column 102. Accordingly, the acrylic acid may be partially included in the acetic acid containing aqueous solution that is discharged through the acetic acid containing aqueous solution transport line 13 in the lower part of the column of the acetic acid absorbing column 102.

In addition, since the acetic acid of the gas that is inputted through the gas input line 16 into the acetic acid absorbing column 102 is absorbed by the process water 12 in the inside of the acetic acid absorbing column 102 and removed, the gas in which the acetic acid is hardly included is discharged through the gas cycle line 18 that is the reaction gas transport line on the upper part of the column of the acetic acid absorbing column 102. The gas cycle line 18 supplies this gas into the reactor so that the gas is capable of being used in the production reaction of the acrylic acid, which is performed in the reactor.

Meanwhile, the acrylic acid containing aqueous solution that is discharged through the lower part of the column of the acrylic acid absorbing column 101 is inputted through the stripping column input line 2 into the stripping column 103. In the stripping column 103, the low boiling point substance that is included in the acrylic acid containing aqueous solution that is inputted into the stripping column 103 is removed. Here, an example of the low boiling point substance that is included in the acrylic acid containing aqueous solution may be acrolein.

The acrylic acid containing aqueous solution in which the low boiling point substance is removed is discharged from the stripping column 103 and is inputted through the azeotropic distillation column input line 3 into the azeotropic distillation column 104.

Since the acrylic acid containing aqueous solution that is inputted into the azeotropic distillation column 104 is distilled under the azeotropic agent of the azeotropic distillation column 104, the azeotropic agent, the water and the acetic acid containing solution are discharged through the upper part of the column of the azeotropic distillation column 104, and the high concentration acrylic acid that hardly includes the water, the acetic acid and the azeotropic agent is discharged through the lower part of the column of the azeotropic distillation column 104.

Here, the azeotropic agent, the water and the acetic acid containing solution that are discharged through the upper part of the column of the azeotropic distillation column 104 is inputted through the phase separator input line 4 into the phase separator 105.

The solution that is inputted into the phase separator 105 is separated into an organic layer that includes the azeotropic agent and a water layer that includes the acetic acid, and here, the organic layer is inputted through the return line 6 that is the azeotropic agent supply line into the azeotropic distillation column 104, and the water layer that includes the acetic acid is discharged to the phase separator discharge line 7. A portion of the acetic acid containing aqueous solution that is discharged to the phase separator discharge line 7 is subjected to the waste water treatment through the waste water treatment line 8, and a portion thereof is supplied through the acetic acid containing aqueous solution transport line 11 into the acrylic acid absorbing column 101 and is reused as the acetic acid containing first absorption solvent.

In addition, the high concentration of acrylic acid that hardly includes the water, the acetic acid and the azeotropic agent that are discharged to the lower part of the column of the azeotropic distillation column 104 is inputted through the high boiling point separation column transport line 5 into the high boiling point separation column 107.

The high concentration of acrylic acid that is inputted into the high boiling point separation column 107 is separated into the crude acrylic acid 9 that is discharged from the high boiling point separation column 107 to the upper part of the column of the high boiling point separation column 107, and the high boiling point impurity 10 that is a waste oil form and is discharged to the lower part of the column of the high boiling point separation column 107.

Here, the crude acrylic acid 9 may be additionally subjected to a deepened purification process for the production of the high purity acrylic acid, and the high boiling point impurity 10 may be introduced into a dimer separator (which is not shown) for efficient configuration of the process.

Figure 2:
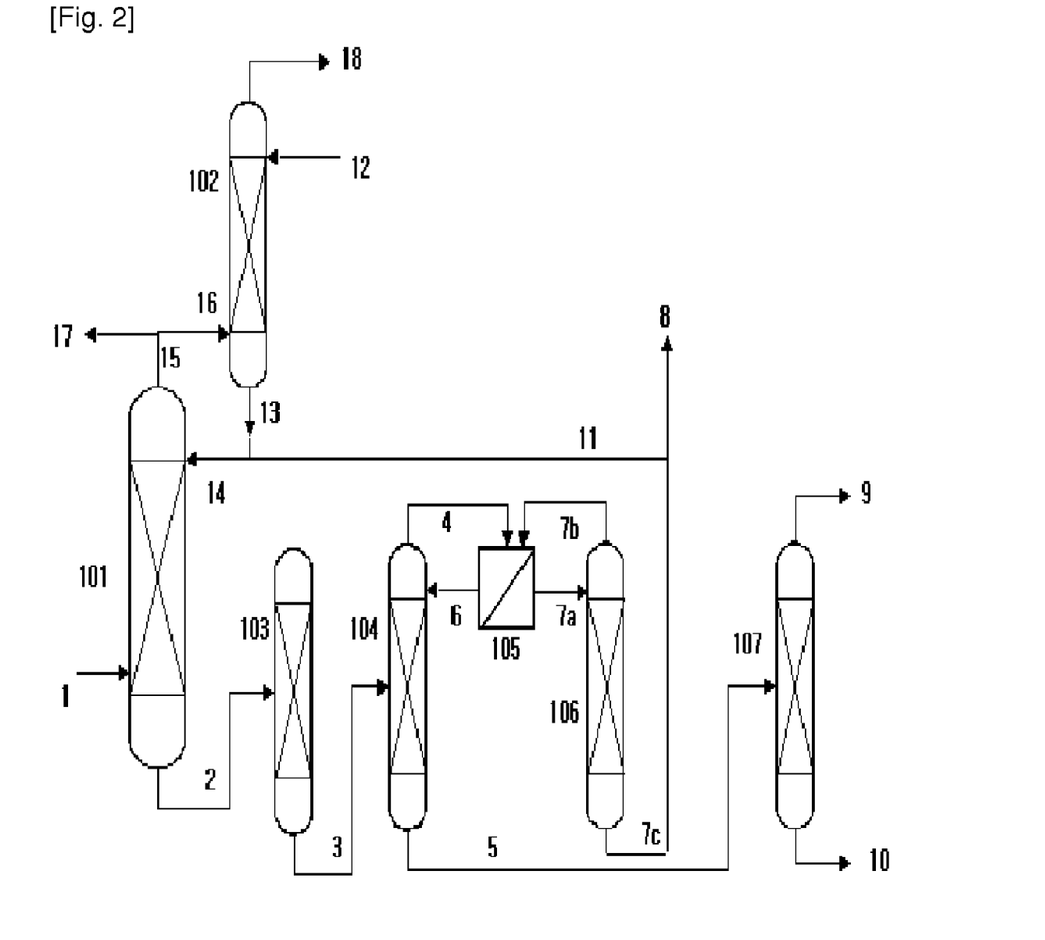
FIG. 2 is a view that schematically illustrates a process for collecting an acrylic acid according to a second embodiment of the present invention.

Meanwhile, in the acrylic acid collecting method according to a second embodiment of the present invention, in the case of when the azeotropic agent is included in the acetic acid containing aqueous solution that is discharged from the phase separator 105, the configuration is the same as that of the first embodiment, except that this is filtered one more in the solvent recovery column 106, and only the filtered azeotropic agent is returned into the phase separator 105. Accordingly, the same configuration as the first embodiment will not be described hereinafter.

As shown in FIG. 2, the solution that is inputted through the phase separator input line 4 into the phase separator 105 is separated into the organic layer that includes the azeotropic agent and the water layer that includes the acetic acid, and here, the organic layer is inputted through the return line 6 into the azeotropic distillation column 104, and the water layer that includes the acetic acid is inputted through the solvent recovery column input line 7a into the solvent recovery column 106.

In the case of when the azeotropic agent is included in the acetic acid containing aqueous solution that is inputted through the solvent recovery column input line 7a into the solvent recovery column 106, the azeotropic agent is discharged to the upper part of the column of the solvent recovery column 106 and is returned through the solvent discharge line 7b that is the azeotropic agent discharge line into the phase separator 105, and the acetic acid containing aqueous solution in which the azeotropic agent is completely removed is discharged through the lower part of the column discharge line 7c of the solvent recovery column 106. Next, a portion of the acetic acid containing aqueous solution that is discharged to the discharge line 7c in the same manner as the first embodiment is subjected to the waste water treatment through the waste water treatment line 8, and a portion thereof is supplied through the acetic acid containing aqueous solution transport line 11 into the acrylic acid absorbing column 101 and is reused as the acetic acid containing first absorption solvent.

MODE FOR THE INVENTION

Hereinafter, the present invention will be described in more detail in light of the Examples, but the present invention is not limited thereto.

Example 1

Azeotropic Distillation Using Toluene (the Concentration of the Acetic Acid Of the Acrylic Acid Aqueous Solution is 2.44%)

The acrylic acid aqueous solution (acrylic acid 65% by weight, acetic acid 2.44% by weight, and water 32.5% by weight) that was obtained by absorbing the acrylic acid mixed gas that was obtained through the propylene oxidation reactor with a water was subjected to the azeotropic distillation on the sieve tray column having the number of tray of 37 and the diameter of 50 mm. The acrylic acid raw material supply tray was the central part of 15th tray, and toluene was introduced as the azeotropic agent at the 2nd tray. While the normal operation was performed, the operation state was the temperature of the upper part of the column of 40.5° C., the temperature of the lower part of the column of 97° C., the pressure of the upper part of the column of 110 torr, the pressure of the lower part of the column of 150 torr, the feed input rate of 6.5 g/min, the toluene input rate of 14.2 g/min. The acrylic acid that was obtained at the lower part of the column included 98.2% by weight of the acrylic acid, 136 ppm of the acetic acid, 557 ppm of water, and 5 ppm of toluene. The composition of the water layer of the distillation solution that was obtained in the upper part of the column was 6.3% by weight of the acetic acid and 1.3% by weight of the acrylic acid.

Example 2

Azeotropic Distillation Using Toluene (the Concentration of the Acetic Acid Of the Acrylic Acid Aqueous Solution is 3.7%)

The same operation as Example 1 was performed, except that the concentration of the acetic acid of the acrylic acid aqueous solution that was introduced into azeotropic distillation column in Example 1 was 3.7%. While the normal operation was performed, the operation state was the temperature of the upper part of the column of 41° C., the temperature of the lower part of the column of 97° C., the pressure of the upper part of the column of 110 torr, the pressure of the lower part of the column of 150 torr, the feed input rate of 6.5 g/min, the toluene input rate of 14.2 g/min. The acrylic acid that was obtained at the lower part of the column included 98.2% by weight of the acrylic acid, 250 ppm of the acetic acid, 400 ppm of water, and 4 ppm of toluene. The composition of the water layer of the distillation solution that was obtained in the upper part of the column was 9.4% by weight of the acetic acid and 0.8% by weight of the acrylic acid.

Example 3

Acrylic Acid Absorbing Column: Acetic Acid Stripping

The product gas that included the acrylic acid that was generated in the propylene oxidation reactor was introduced into the lower part of the acrylic acid absorbing column in which gauze packings were packed and which had the inner diameter of 70 mm and the height of 1050 mm at a flow rate of 145 L/min. At the upper part of the acrylic acid absorbing column, 9% acetic acid aqueous solution was sprayed as the acrylic acid absorption solvent at the rate of 16 g/min in a spray manner. The concentration of the acetic acid aqueous solution was set in consideration of the concentration of the acetic acid of the upper condensates of the azeotropic distillation column and the concentration of the acetic acid of the acetic acid aqueous solution that was discharged to the lower part of the acrylic acid absorbing column. The temperature of the upper part of the acrylic acid absorbing column was controlled to 64° C., and at this temperature, the gas in which moisture was saturated was discharged to the upper part of the acrylic acid absorbing column. At this time, the amount of the acetic acid that was stripped to the upper part of the acrylic acid absorbing column was the level in which 69% of the acetic acid that was included in the acetic acid aqueous solution added to the acrylic acid absorbing column as the acrylic acid absorption solvent was removed, and the concentration of the acetic acid of the gas that was discharged to the upper part of the acrylic acid absorbing column was 2500 ppmv.

Example 4

Acrylic Acid Absorbing Column: Acetic Acid Stripping

The same operation as Example 3 was performed, except that the concentration of the acetic acid aqueous solution that was supplied to the upper part of the acrylic acid absorbing column in Example 3 was 12%. At this time, the amount of the acetic acid that was stripped to the upper part of the acrylic acid absorbing column was the level in which 67% of the acetic acid that was included in the acetic acid aqueous solution added to the acrylic acid absorbing column as the acrylic acid absorption solvent was removed, and the concentration of the acetic acid of the gas that was discharged to the upper part of the acrylic acid absorbing column was 3200 ppmv.

Example 5

The Removal of the Acetic Acid in the Acetic Acid Absorbing Column

From a portion of the gas that was discharged from the upper part of the acrylic acid absorbing column, the acetic acid was removed through the acetic acid absorbing column, and the acetic acid free gas was recycled into the reactor. The absorbing column in which gauze packings were packed and which had the inner diameter of 70 mm and the height of 1050 mm was used as the acetic acid absorbing column. At the lower part of the acetic acid absorbing column, the $N_2$ gas that included the 64C saturated steam in which the concentration of the acetic acid was 2500 ppmv was introduced at the rate of 70 L/min, and at the upper part of the acetic acid absorbing column, in order to absorb the acetic acid, the process water was sprayed at the rate of 15 g/min in a spray manner. The temperature of the upper part of the column of the acetic acid absorbing column was maintained at 63° C. At this time, the concentration of the acetic acid of the gas that was discharged to the upper part of the acetic acid absorbing column was 320 ppmv, and was the level in which 88% of the acetic acid that was included in the gas introduced to the lower part of the acetic acid absorbing column was removed.

Example 6

The Removal of the Acetic Acid in the Acetic Acid Absorbing Column

The same operation as Example 5 was performed, except that the flow rate of the process water that was supplied to the upper part of the acetic acid absorbing column in Example 5 was 20 g/min. At this time, the concentration of the acetic acid of the gas that was discharged to the upper part of the acetic acid absorbing column was 230 ppmv, and was the level in which 91% of the acetic acid that was included in the gas introduced to the lower part of the acetic acid absorbing column was removed.

Example 7

The Removal of the Acetic Acid in the Acetic Acid Absorbing Column

The same operation as Example 5 was performed, except that the concentration of the acetic acid of the gas that was introduced into the lower part of the acetic acid absorbing column in Example 5 was increased to 3200 ppmv and the flow rate of the process water that was supplied to the upper part of the acetic acid absorbing column was 15 g/min. At this time, the concentration of the acetic acid of the gas that was discharged to the upper part of the acetic acid absorbing column was 270 ppmv, and was the level in which 91% of the acetic acid that was included in the gas introduced to the lower part of the acetic acid absorbing column was removed.

Example 8

The Removal of the Acetic Acid in the Acetic Acid Absorbing Column

The same operation as Example 5 was performed, except that the concentration of the acetic acid of the gas that was introduced into the lower part of the acetic acid absorbing column in Example 5 was increased to 3200 ppmv and the flow rate of the process water that was supplied to the upper part of the acetic acid absorbing column was 20 g/min. At this time, the concentration of the acetic acid of the gas that was discharged to the upper part of the acetic acid absorbing column was 220 ppmv, and was the level in which 93% of the acetic acid that was included in the gas introduced to the lower part of the acetic acid absorbing column was removed.

Example 9

The Oxidation Reaction of Propylene

As the fixed bed tubular reactor for the oxidation reaction of propylene, the fixed bed tubular reactor that had the inner diameter of the contact tube in the reactor of 26 mm and the wall thickness of the contact tube of 2 mm was used.

The packing of the catalyst in the contact tube of the fixed bed tubular reactor was performed so that the inactive substance layer (alumina) having the size of 755 mm, the first stage catalyst having the size of 3000 mm, the inactive substance layer having the size of 2000 mm, and the second stage catalyst having the size of 3000 mm were sequentially packed from the entrance of the reaction gas.

Here, as the first stage catalyst, the catalyst of Korean Registered Patent No. 0349602, which was based on molybdenum (Mo) and bismuth (Bi), was used. As the second stage catalyst, the catalyst of Korean Registered Patent No. 0378018, which was based on molybdenum (Mo) and vanadium (V), was used.

In addition, in the case of the fixed bed tubular reactor, since the thermal conduction protection tube in the contact tube of the fixed bed tubular reactor was installed at the middle of the contact tube, the tube was configured so as to measure the temperature of the entire region of the reactor. The temperature of the external wall of the contact tube was configured so as to be independently controlled according to the step through the melted and cycled salt, thus the temperature of the contact tube was constantly maintained through the cycling of the melted salt, and the reaction gas that included the raw material was inputted into the contact tube of the reactor through the lower part of the reactor.

Here, before the reaction gas that was inputted into the contact tube was inputted into the reactor, the reaction gas was sufficiently heated by a preliminary heating device to increase the temperature thereof, and then inputted into the reactor.

The concentration of propylene of the reaction gas was 7.5%, the concentration of $O_2$ was 14.8%, the moar ratio of $O_2/C_3$ was 1.97, the space velocities of the first stage and the second stage catalysts were respectively maintained to 1260 $hr^{-1}$ and 1400 $hr^{-1}$. At this time, the temperature of the external wall of the first stage reactor was in the range of 300~310° C., and the temperature of the external wall of the second stage reactor was in the range of 260~270° C.

All the conditions were the same as each other, in the reaction gas in which the gas including the steam that was discharged to the upper part of the acetic acid absorbing column in Example 8 was mixed, in the case of when the concentration of moisture of the reaction gas was 7.5%, the temperature of the hot spot of the first stage catalyst was 383° C., the temperature of the hot spot of the second stage catalyst was 327° C., and the yield of the acrylic acid was 84.7%.

Example 10

The Oxidation Reaction of Propylene

The same process as Example 9 was performed, except that in the reaction gas in which the gas including the steam that was discharged to the upper part of the acetic acid absorbing column in Example 8 was mixed, the concentration of moisture of the reaction gas was 10%. Thereby, the temperature of the hot spot of the first stage catalyst was 373° C., the temperature of the hot spot of the second stage catalyst was 323° C., and the yield of the acrylic acid was increased to 85.3%.

As described above, according to the present invention, in the case of when the organic byproduct containing solution was used as the absorption solvent that was used in order to obtain the (meth)acrylic acid that was included in the organic byproduct and (meth)acrylic acid containing mixed gas in a (meth)acrylic acid containing solution, it can be seen that the yield ratio of the (meth)acrylic acid was increased.

In addition, after the organic byproduct that was included in the organic byproduct containing gas was sufficiently removed, it was supplied into the reactor in which the production reaction of the (meth)acrylic acid was performed to participate in the production reaction of the (meth)acrylic acid. Thus, in the case of when the gas in which the conventional organic byproduct was not sufficiently removed was supplied into the reactor, the occurrence of the process troubles was prevented by the organic byproduct that was included in the gas.

In addition, in the production reactor of the (meth)acrylic acid, during the production of the (meth)acrylic acid by using the catalyst, in the case of the used catalyst, the moisture is required in order to perform the stable operation. At this time, in the gas that includes the organic byproduct and the steam, the organic byproduct is sufficiently removed, and since the gas including the moisture is capable of being supplied into the production reactor of the (meth)acrylic acid, the steam type of process water that is added to the initial reactor can be saved. In addition, in the catalyst in the reactor, a spot in which the temperature is abnormally high or heat accumulation is relatively high, that is, a hot spot may occur. This hot spot is capable of being reduced to improve the stability of the catalyst and to improve the reaction yield.

The invention claimed is:

1. A (meth)acrylic acid collecting method for collecting a (meth)acrylic acid from a mixed gas that includes an organic byproduct, a steam and a (meth)acrylic acid that are prepared in a production reaction of the (meth)acrylic acid, wherein the (meth)acrylic acid collecting method comprises the steps of:
   a) contacting the mixed gas that includes the organic byproduct, the steam, and the (meth)acrylic acid with a (meth)acrylic acid absorption solvent, to obtain a (meth)acrylic acid containing solution and a gas that includes the organic byproduct and the steam while the gas and the (meth)acrylic acid containing solution are separated from each other, the (meth acrylic acid absorption solvent includes the organic byproduct at a concentration of 9 to 12%;
   b) contacting the gas that includes the organic byproduct and the steam obtained in the step a) with the organic byproduct absorption solvent, to obtain an organic byproduct containing solution and a gas that includes the steam and while the gas and the organic byproduct containing solution are separated from each other;
   c) supplying the gas that includes the steam obtained in the step b) into the production reaction of the (meth)acrylic acid; and
   d) obtaining the (meth)acrylic acid and the organic byproduct containing solution from the (meth)acrylic acid containing solution obtained in the step a), and
   wherein the method further comprises a step of supplying the organic byproduct containing solution that is obtained in the steps b) and d) into the step a), so as to be used as the (meth)acrylic acid absorption solvent of the step a).

2. The (meth)acrylic acid collecting method as set forth in claim 1, wherein the (meth)acrylic acid containing solution obtained in the step a) is supplied into a stripping column to remove a low boiling point substance and then is supplied into the step d), in case that the low boiling point substance is included in the (meth)acrylic acid containing solution obtained in the step a).

3. The (met)acrylic acid collecting method as set forth in claim 1, wherein the concentration of the unseparated organic byproduct in the gas including the steam obtained in the step b) is in the range of 0 to 1000 ppmv, in case that the unseparated organic byproduct is contained in the gas including the steam in the step b).

4. The (meth)acrylic acid collecting method as set forth in claim 1, wherein the production reaction of the (meth)acrylic acid is performed in a reactor in which one or more reactants selected from the group consisting of propane, propylene, isobutylene, t-butylene, butane and (meth)acrolein are subjected to the oxidation reaction under the catalyst, and in the step c), the gas that includes the steam obtained in the step b) is supplied into the reactor.

5. The (meth)acrylic acid collecting method as set forth in claim 1, wherein, in the step d), the (meth)acrylic acid containing solution obtained in the step a) is separated into the organic byproduct containing solution and the (meth)acrylic acid by a distillation method, in case that the unseparated organic byproduct is contained in the (meth)acrylic acid containing solution obtained in the step a).

6. The (meth)acrylic acid collecting method as set forth in claim 5, wherein, in case that an azeotropic agent is included in the organic byproduct containing solution obtained in the step d) and the distillation method of step d) is performed in azeotropic distillation column supplied by an azeotropic agent, the method further comprises the steps of:
   supplying the organic byproduct containing solution obtained in the step d) from the azeotropic distillation column to a phase separator to separate the azeotropic agent from the organic byproduct containing solution; and
   supplying the organic byproduct containing solution which the azeotropic agent is separated from, into the step a) to be used as the (meth)acrylic acid absorption solvent of the step a).

7. The (meth)acrylic acid collecting method as set forth in claim 6, wherein, the organic byproduct containing solution is further treated to remove the unseparated azeotropic agent in a solvent recovery column, and then is supplied into the step a), in case that the unseparated azeotropic agent is included in the organic byproduct containing solution discharged from the phase separator.

8. The (meth)acrylic acid collecting method as set forth in claim 1, wherein the method further comprises a step of supplying the (meth)acrylic acid obtained in the step d) into a high boiling point separation column to remove the high boiling point impurity, in case that the high boiling point impurity is included in the (meth)acrylic acid obtained in the step d).

9. A (meth)acrylic acid collecting device for collecting a (meth)acrylic acid from a mixed gas that includes an organic byproduct, a steam, and a (meth)acrylic acid that are prepared in a reactor for producing the (meth)acrylic acid, wherein the (meth)acrylic acid collecting device comprises:
   a (meth)acrylic acid absorbing column that is connected to the reactor, and separates a (meth)acrylic acid containing solution and a gas including the organic byproduct and the steam by contacting the mixed gas including the organic byproduct, the steam, and the (meth)acrylic acid that are discharged from the reactor, with a (meth)acrylic acid absorption solvent;
   an organic byproduct absorbing column that is connected to the (meth)acrylic acid absorbing column, and separates an organic byproduct containing solution and a gas including the steam by contacting the gas including the organic byproduct and the steam that are discharged from the (meth)acrylic acid absorbing column, with the organic byproduct absorption solvent;

a reaction gas transport line that connects the organic byproduct absorbing column and the reactor and transports the gas including the steam that is discharged from the organic byproduct absorbing column to the reactor so that the gas including the steam is used as a reaction gas for production of the (meth)acrylic acid in the reactor; and a (meth)acrylic acid separating device that is connected to the (meth)acrylic acid absorbing column and separates the (meth)acrylic acid from the (meth)acrylic acid containing solution that is discharged from the (meth)acrylic acid absorbing column, and a (meth)acrylic acid absorption solvent supply line that connects the organic byproduct absorbing column to the (meth)acrylic acid absorbing column and supplies the organic byproduct containing solution that is discharged from the organic byproduct absorbing column, into the (meth)acrylic acid absorbing column so that the organic byproduct containing solution is used as the (meth)acrylic acid absorption solvent in the (meth)acrylic acid absorbing column, and wherein the (meth)acrylic acid absorption solvent comprises the organic byproduct at a concentration of 9 to 12%.

10. The (meth)acrylic acid collecting device as set forth in claim 9, further comprising:

a stripping column that is positioned between the (meth)acrylic acid absorbing column and the (meth)acrylic acid separating device, and that strips a low boiling point substance from the (met)acrylic acid containing solution discharged from the (meth)acrylic acid absorbing column to supply the (meth)acrylic acid containing solution into the (meth)acrylic acid separating device, in case that the low boiling point substance is included in the (meth)acrylic acid containing solution discharged from the (meth)acrylic acid absorbing column.

11. The (meth)acrylic acid collecting device as set forth in claim 9, wherein the (meth)acrylic acid separating device comprises an azeotropic distillation column using the azeotropic agent which separates the (meth)acrylic acid containing solution discharged from the (meth)acrylic acid absorbing column into the organic byproduct containing solution and the (meth)acrylic acid, in case that unseparated organic byproduct is included in the (meth)acrylic acid containing solution discharged from the (meth)acrylic acid absorbing column.

12. The (meth)acrylic acid collecting device as set forth in claim 11, further comprising:

a phase separator that is connected to the azeotropic distillation column and separates the azeotropic agent from the organic byproduct containing solution discharged from the azeotropic distillation column, in case that the unseparated azeotropic agent is included in the organic byproduct containing solution discharged from the azeotropic distillation column; and a (meth)acrylic acid absorption solvent supply line that connects the phase separator to the (meth)acrylic acid absorbing column, and supplies the organic byproduct containing solution discharged from the phase separator into the (meth)acrylic acid absorbing column so that the organic byproduct containing solution discharged from the phase separator is used as the (meth)acrylic acid absorption solvent in the (meth)acrylic acid absorbing column.

13. The (meth)acrylic acid collecting device as set forth in claim 12, further comprising:

a solvent recovery column that is positioned between the phase separator and the (meth)acrylic acid absorbing column, and that removes the unseparated azeotropic agent that is included in the organic byproduct containing solution discharged from the phase separator and then supplies the organic byproduct containing solution into the (meth)acrylic acid absorbing column, in case that the unseparated azeotropic agent is included in the organic byproduct containing solution discharged from the phase separator.

14. The (meth)acrylic acid collecting device as set forth in claim 9, further comprising:

a high boiling point separation column that is connected to the (meth)acrylic acid separating device, and removes a high boiling point impurity from the (meth)acrylic acid discharged from the (meth)acrylic acid separating device, in case that the high boiling point impurity is included in the (meth)acrylic acid discharged from the (meth)acrylic acid separating device.

* * * * *